United States Patent
Ji et al.

(10) Patent No.: US 11,135,254 B2
(45) Date of Patent: Oct. 5, 2021

(54) BIFIDOBACTERIUM LONGUM RAPO STRAIN FOR ALLEVIATING, TREATING OR PREVENTING RHEUMATOID ARTHRITIS AND COMPOSITION CONTAINING THE SAME

(71) Applicants: BIFIDO CO., LTD., Gangwon-do (KR); THE CATHOLIC UNIVERSITY OF KOREA INDUSTRY-ACADEMIC COOPERATION FOUNDATION, Seoul (KR)

(72) Inventors: Geun Eog Ji, Seoul (KR); Yun Ju Jeong, Seoul (KR); Sang Jun Park, Seoul (KR); Su Young Yang, Seoul (KR); Hyon Ha Lee, Seoul (KR); Sung Hwan Park, Seoul (KR); Mi La Cho, Seoul (KR); Ji Hyeon Ju, Seoul (KR); Seung Ki Kwok, Seoul (KR); Joo Ha Lee, Seoul (KR); Ji Won Kim, Seoul (KR); Seon Yeong Lee, Seoul (KR); Jun Geol Ryu, Seoul (KR); Joo Yeon Jhun, Seoul (KR); Jae Yoon Ryu, Seoul (KR)

(73) Assignees: THE CATHOLIC UNIVERSITY OF KOREA, Seoul (KR); BIFIDO CO., LTD., Hongcheon-gun (KR)

( * ) Notice: Subject to any disclaimer, the term of this patent is extended or adjusted under 35 U.S.C. 154(b) by 0 days.

(21) Appl. No.: 16/647,355

(22) PCT Filed: Oct. 15, 2019

(86) PCT No.: PCT/KR2019/013499
§ 371 (c)(1),
(2) Date: Mar. 13, 2020

(87) PCT Pub. No.: WO2020/122396
PCT Pub. Date: Jun. 18, 2020

(65) Prior Publication Data
US 2021/0154244 A1 May 27, 2021

(30) Foreign Application Priority Data
Dec. 12, 2018 (KR) .......................... 10-2018-0160170

(51) Int. Cl.
*A61K 35/745* (2015.01)
*A23L 33/135* (2016.01)
*A61P 29/00* (2006.01)

(52) U.S. Cl.
CPC .......... *A61K 35/745* (2013.01); *A23L 33/135* (2016.08); *A61P 29/00* (2018.01)

(58) Field of Classification Search
None
See application file for complete search history.

(56) References Cited

U.S. PATENT DOCUMENTS

| 2003/0170217 A1 | 9/2003 | Collins et al. |
| 2009/0170772 A1 | 7/2009 | Iwabuchi et al. |
| 2017/0058270 A1 | 3/2017 | Garcia-Garcia et al. |

FOREIGN PATENT DOCUMENTS

| KR | 10-2014-0006509 A | 1/2014 |
| KR | 10-1355440 B1 | 2/2014 |
| KR | 10-2018-0008358 A | 1/2018 |
| KR | 10-2018-0089324 A | 8/2018 |
| KR | 10-2018-0103772 A | 9/2018 |

OTHER PUBLICATIONS

Sajan Chandrangadhan Achi et al.; "Prophylactic effects of probiotic *Bifidobacterium* spp. in the resolution of inflammation in arthritic rats"; Applied Microbial and Cell Physiology; 2019; [Electronic Publication on Jun. 5, 2019], vol. 103, pp. 6287-6296.

A.T. Vieira et al.; Oral treatment with *Bifidobacterium longum* $5^{1A}$ reduced inflammation in a murine experimental model of gout ; Beneficial Microbes, 2015, vol. 6, No. 6, pp. 799-806.

Elnaz Vaghef-Mehrabany et al., "Effects of probiotic supplementation on lipid profile of woman with rheumatoid arthritis: A randomized placebo-controlled clinical trial"; Health Promotion Perspectives; 2017, vol. 7, No. 2, pp. 95-101.

International Search Report dated Mar. 20, 2020 for International Application No. PCT/KR2019/013499.

*Primary Examiner* — Brian Gangle
(74) *Attorney, Agent, or Firm* — Sughrue Mion, PLLC

(57) ABSTRACT

Disclosed are a novel *Bifidobacterium longum* RAPO (Accession No.: KCTC 13773BP) and a composition for alleviating, treating or preventing rheumatoid arthritis containing *Bifidobacterium longum* RAPO (Accession No.: KCTC 13773BP) selected herein.

3 Claims, 11 Drawing Sheets

BIFIDOBACTERIUM LONGUM RAPO STRAIN FOR ALLEVIATING, TREATING OR PREVENTING RHEUMATOID ARTHRITIS AND COMPOSITION CONTAINING THE SAME

TECHNICAL FIELD

The present invention relates to a novel *Bifidobacterium longum* RAPO (Accession No.: KCTC 13773BP) and more specifically to *Bifidobacterium longum* RAPO (Accession No.: KCTC 13773BP) and a composition for alleviating, treating or preventing rheumatoid arthritis containing the same.

BACKGROUND ART

Rheumatoid arthritis is a chronic inflammatory disease of unknown cause, characterized by multiple arthritis. An initial symptom thereof is inflammation of the synovial membrane surrounding a joint, but inflammation gradually spreads to adjacent cartilage and bones, causing destruction and deformation of the joint. Rheumatoid arthritis has not only articular symptoms, but also abarticular symptoms such as anemia, dryness, subcutaneous nodules, pulmonary fibrosis, vasculitis and skin ulcers, and thus may be considered a serious disease that can invade the whole body.

Drugs used for rheumatoid arthritis include nonsteroidal anti-inflammatory drugs, steroids, antirheumatic drugs, TNF blockers and the like. It is known that nonsteroidal anti-inflammatory drugs and steroids can alleviate the symptoms of the disease by reducing inflammation, but cannot inhibit the progression of the disease. These drugs have limited usefulness as effective treatments due to problems such as gastrointestinal disorders and side effects upon long-term use.

Accordingly, there is a need to develop new therapeutic agents with excellent functionality and safety while overcoming the limitations of conventional treatment methods.

DISCLOSURE

Technical Problem

Therefore, the present invention has been made in view of the above problems, and it is one object of the present invention to select a strain having excellent effects in alleviating, preventing or treating rheumatoid arthritis, and to develop and provide a composition containing the same.

Technical Solution

In accordance with the present invention, the above and other objects can be accomplished by the provision of *Bifidobacterium longum* RAPO (Accession No.: KCTC 13773BP) capable of preventing or treating rheumatoid arthritis.

In accordance with another aspect, provided is a food composition for alleviating rheumatoid arthritis containing at least one selected from the group consisting of a culture solution of *Bifidobacterium longum* RAPO (Accession No.: KCTC 13773BP), a concentrate of the culture solution and a dry powder of the culture solution.

In the food composition of the present invention, the food composition may preferably be any one selected from lactic-acid-bacteria-fermented milk, soy milk, milk powders, yogurts, beverages, granules and dietary supplements.

In accordance with another aspect, provided is a pharmaceutical composition for preventing or treating rheumatoid arthritis containing at least one selected from the group consisting of a culture solution of *Bifidobacterium longum* RAPO (Accession No.: KCTC 13773BP), a concentrate of the culture solution and a dry powder of the culture solution.

Advantageous Effects

The present invention provides a composition for alleviating, treating or preventing rheumatoid arthritis containing *Bifidobacterium longum* RAPO (Accession No.: KCTC 13773BP).

RAPO, MTX: methotrexate (MTX)-administered group, *B. longum* RAPO: *Bifidobacterium longum* RAPO-administered group).

Figure 9:
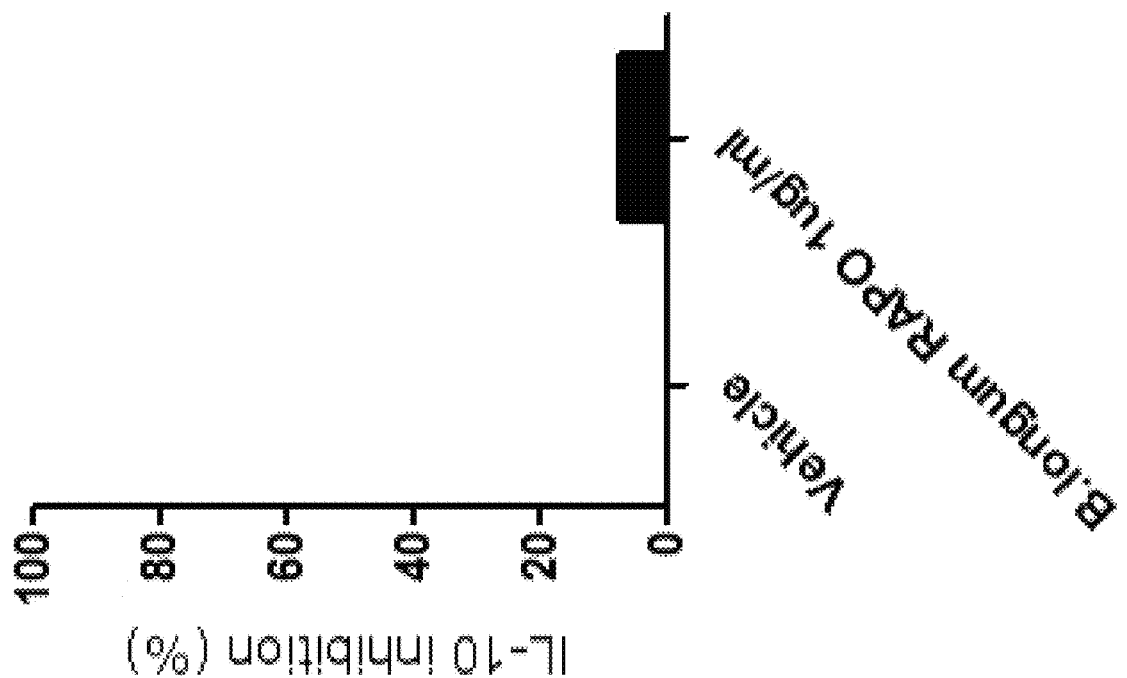
Figure 9:
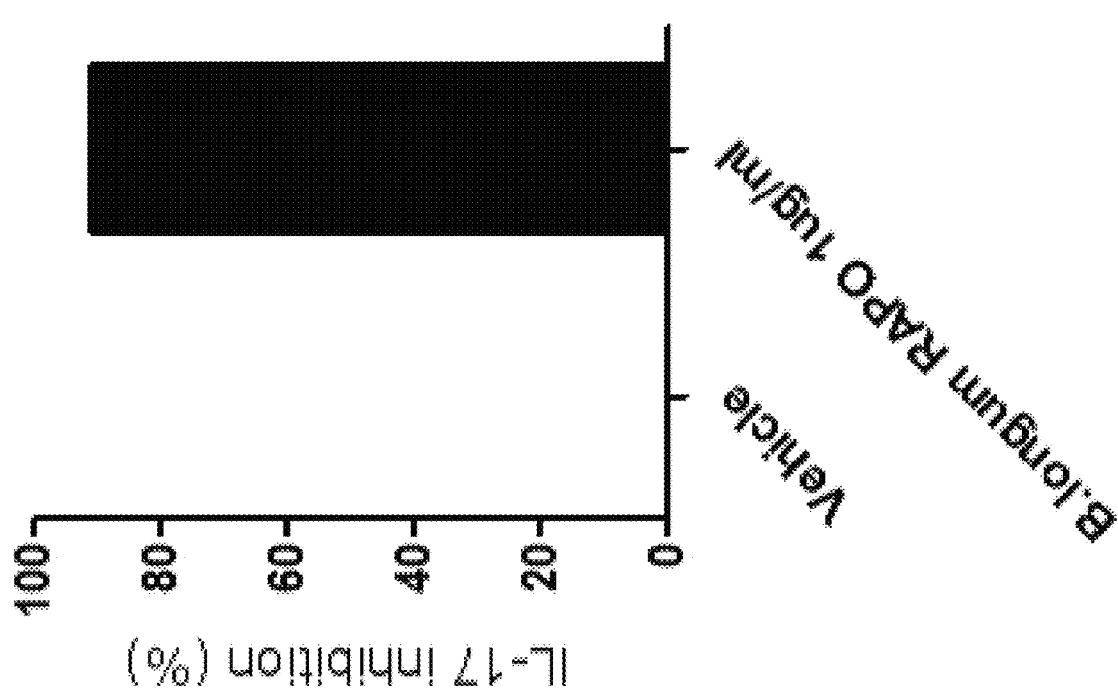

FIG. 9 is a graph showing the result of determination of the human immune cell regulation capability of *Bifidobacterium longum* RAPO (Accession No.: KCTC 13773BP) identified in the present invention, wherein the graph shows the cytokine inhibition rate of *Bifidobacterium longum* RAPO of the present invention, based on the expression levels, measured by ELISA, of inflammatory cytokine IL-17 and anti-inflammatory cytokine IL-10.

Figure 10:
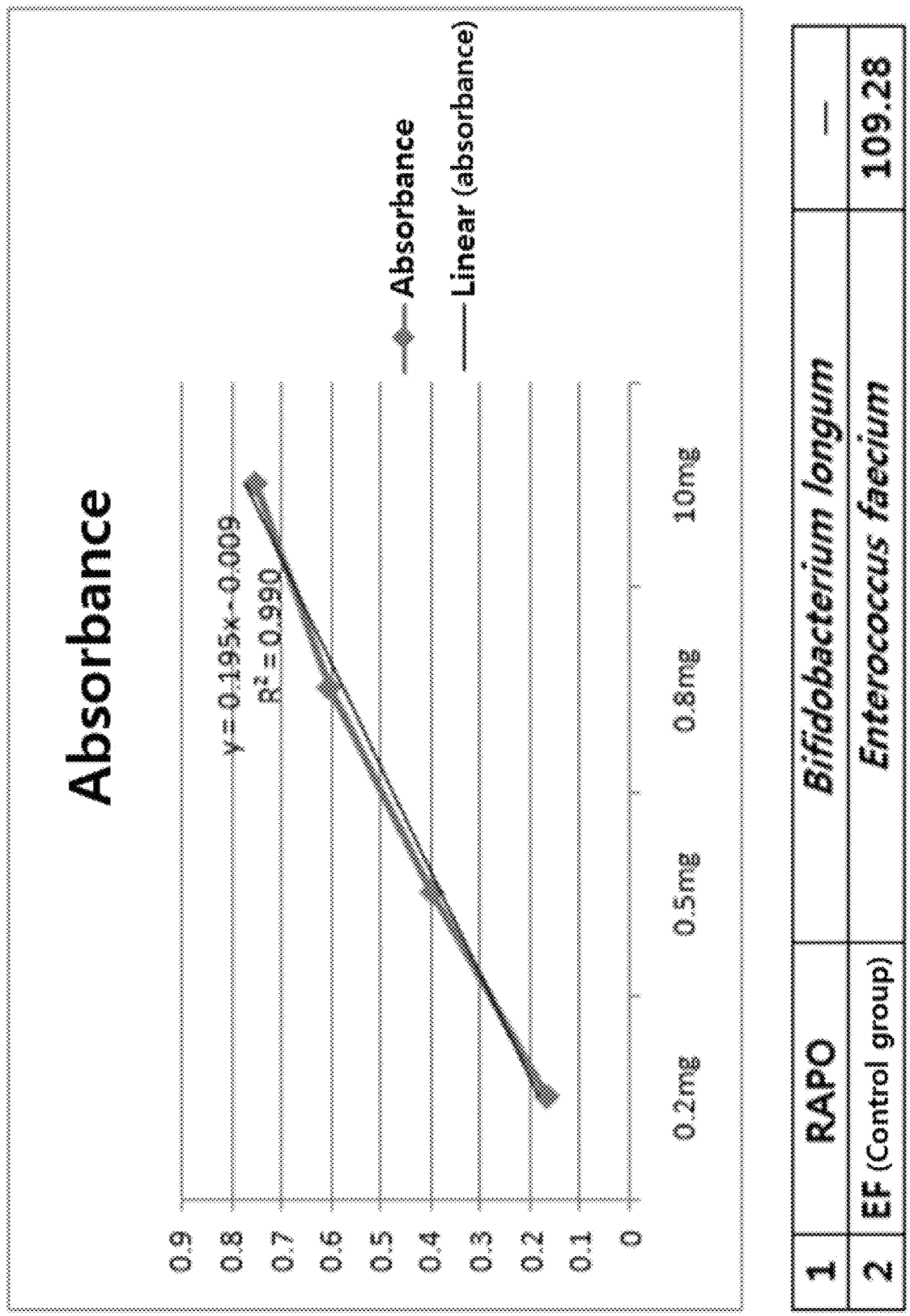

FIG. 10 is a graph showing the result of quantification of the amount of ammonia produced using an indophenol method for measuring the ammonia production ability of *Bifidobacterium longum* RAPO (Accession No.: KCTC 13773BP) identified in the present invention. *Enterococcus faecium* was used as a positive control group for comparison.

Figure 11:
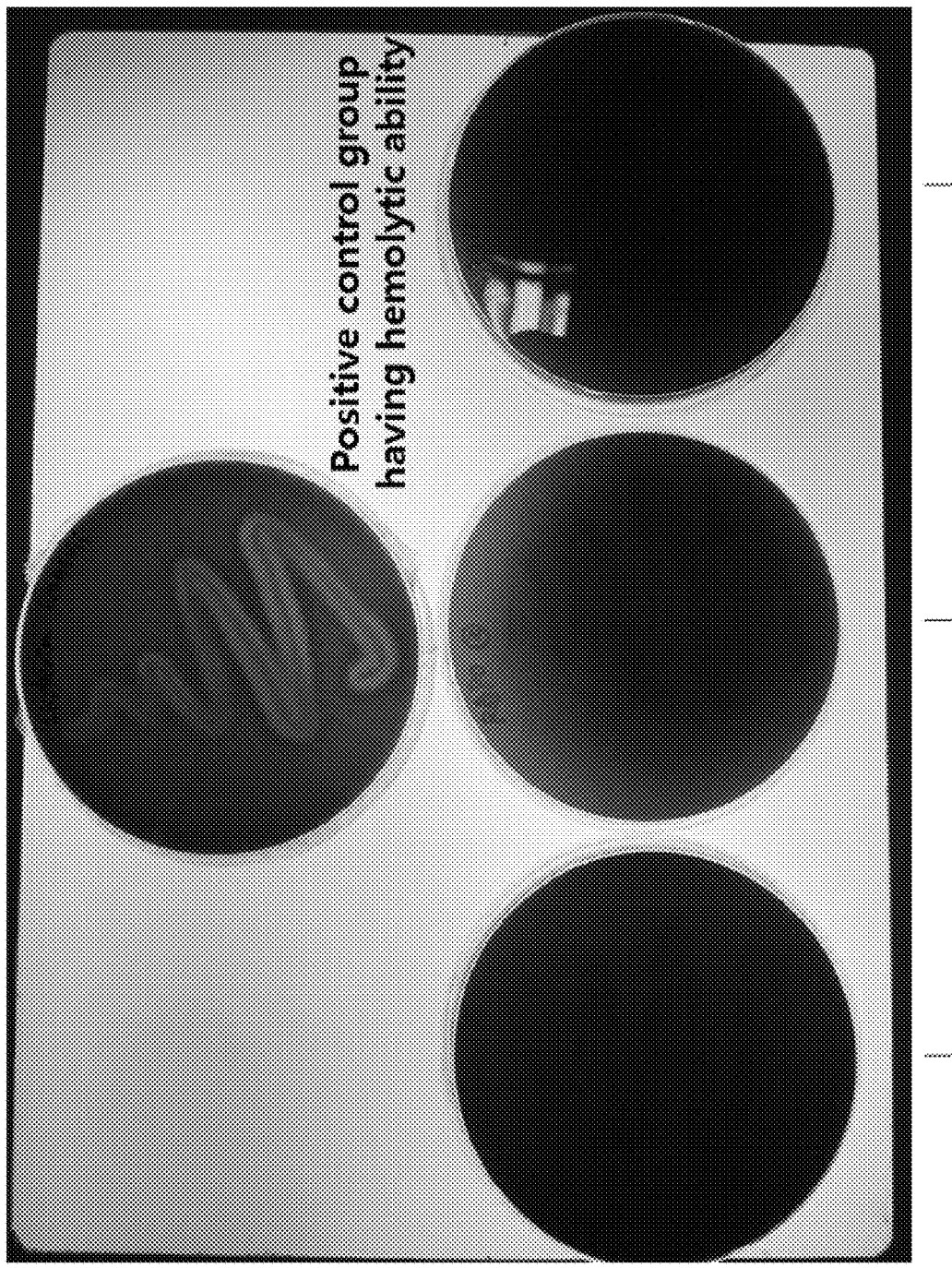

FIG. 11 is an image showing the hemolytic ability of *Bifidobacterium longum* RAPO (Accession No.: KCTC 13773BP) identified in the present invention. Experiments were repeated in triplicate, and *Listeria ivanovii* was used as a positive control group for comparison.

BEST MODE

In one aspect, the present invention is directed to *Bifidobacterium longum* RAPO (Accession No.: KCTC 13773BP) capable of preventing or treating rheumatoid arthritis.

In the present invention, the genus *Bifidobacterium*, which belongs to the phylum *Actinobacteria*, was recovered through next-generation sequencing using human feces samples as specimens. Among the recovered several species of *Bifidobacterium*, *Bifidobacterium longum* RAPO showing the best result in in-vitro experiments related to the expression rate of cytokines, which are the cause of rheumatoid arthritis, was selected and was provided as a strain having excellent efficacy in alleviating, treating or preventing rheumatoid arthritis.

The following experiment demonstrated that the strain of the present invention has an effect of controlling rheumatoid arthritis diseases by significantly inhibiting the onset and incidence of rheumatoid arthritis, and has an effect of controlling the destruction of rheumatoid arthritis joint tissue by reducing the degree of inflammation and the degree of the destruction of bone and cartilage. In addition, the strain causes only slight damage to the colorectal tissue of mice, has a high rate of inhibition of the inflammatory cytokine IL-17 affecting the onset of rheumatoid arthritis, and low ammonia production and low hemolytic ability, which means that the strain can be used as a strain that is safe and effective for alleviating, preventing or treating rheumatoid arthritis, and food and pharmaceutical compositions containing the same can be provided.

In another aspect, the present invention is directed to a food composition for alleviating rheumatoid arthritis containing at least one selected from the group consisting of a culture solution of *Bifidobacterium longum* RAPO (Accession No.: KCTC 13773BP), a concentrate of the culture solution, and a dry powder of the culture solution.

In the food composition of the present invention, the food composition may, for example, include any one selected from meat, cereals, caffeinated beverages, general beverages, chocolate, breads, snacks, confectioneries, candy, pizza, jelly, noodles, gums, dairy products, ice cream, alcoholic beverages, liquors, vitamin complexes and other health supplements. More preferably, the food composition may include any one selected from lactic-acid-bacteria-fermented milk, soy milk, powdered milk, yogurt, beverages, granules and health supplements, but is not necessarily limited thereto.

In another aspect, the present invention is directed to a pharmaceutical composition for preventing or treating rheumatoid arthritis containing, as an active ingredient, at least one selected from the group consisting of a culture solution of *Bifidobacterium longum* RAPO (Accession No.: KCTC 13773BP), a concentrate of the culture solution, and a dry powder of the culture solution.

Meanwhile, the pharmaceutical composition of the present invention may further include a pharmaceutically acceptable carrier, diluent or excipient. The carrier, excipient or diluent that can be used in the present invention includes lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinylpyrrolidone, water, methylhydroxybenzoate, propylhydroxybenzoate, talc, magnesium stearate and mineral oils, and one or more selected therefrom may be used. In addition, when the therapeutic and preventive agent is a drug, it may further include a filler, an anti-coagulant, a lubricant, a wetting agent, a fragrance, an emulsifier or a preservative.

Meanwhile, the formulation of the pharmaceutical composition according to the present invention may be prepared in a suitable form depending on the method of use, and may be prepared in accordance with a method well-known in the art to provide rapid, sustained or delayed release of the active ingredient, particularly after administration to a mammal. Specific examples of the formulation include at least one selected from plasters, granules, lotions, liniments, lemonades, aromatic waters, powders, syrups, ophthalmic ointments, liquids and solutions, aerosols, extracts, elixirs, ointments, fluid extracts, emulsions, suspensions, decoctions, infusions, ophthalmic solutions, tablets, suppositories, injections, spirits, cataplasma, capsules, creams, troches, tinctures, pastes, pills, and soft or hard gelatin capsules.

Meanwhile, in the pharmaceutical composition of the present invention, the dosage may be determined in consideration of the administration method, the age, gender and weight of the patient, and the severity of the disease. For example, the pharmaceutical composition may be orally administered one or more times at 0.00001 to 100 mg/kg (body weight) of the active ingredient per day. However, the dosage is merely an example for illustration, and may be changed depending on the condition of the patient and the physician's prescription.

Mode for Invention

Hereinafter, the present invention will be described in more detail with reference to the following examples, but the scope of the present invention is not limited to the examples, and includes variations and technical concepts equivalent thereto.

Example 1: Detection of *Bifidobacterium longum* RAPO (Accession No.: KCTC 13773BP)

Rheumatoid factor (RF), which is a type of autoantibody in the Fc region of IgG, is found in 80% of patients with rheumatoid arthritis. Therefore, in the present embodiment, the intestinal flora distribution depending on the presence and degree of rheumatoid factor was analyzed at the phylum and genus levels to detect microorganisms effective for treating rheumatoid arthritis.

1) Sample Preparation and Analysis Method

In order to analyze the distribution of microbiomes depending on the rheumatoid factor (RF), an autoantibody found in 80% of patients with rheumatoid arthritis, the age of patients with rheumatoid arthritis was limited to 40 to 59 years old, the fecal samples were collected from 17, 24 and 50 patients for RF-negative (0~20), low-positive (20<RF≤60) and high-positive (>60) groups, respectively, and stored at −80° C. RF was also analyzed as a positive including low positive and high positive, and a negative. Then, in order to perform next-generation sequencing using fecal samples, bacterial genomic DNA was isolated from the samples, and 16S rRNA genes specific to microorganisms were amplified to produce a library. The nucleotide sequences of 16S rRNA genes from the library were decoded using Miseq from Illumina. The decoded sequences were subjected to bioinformatics analysis using Q11ME191 (an open-source bioinformatic pipeline).

Figure 1:
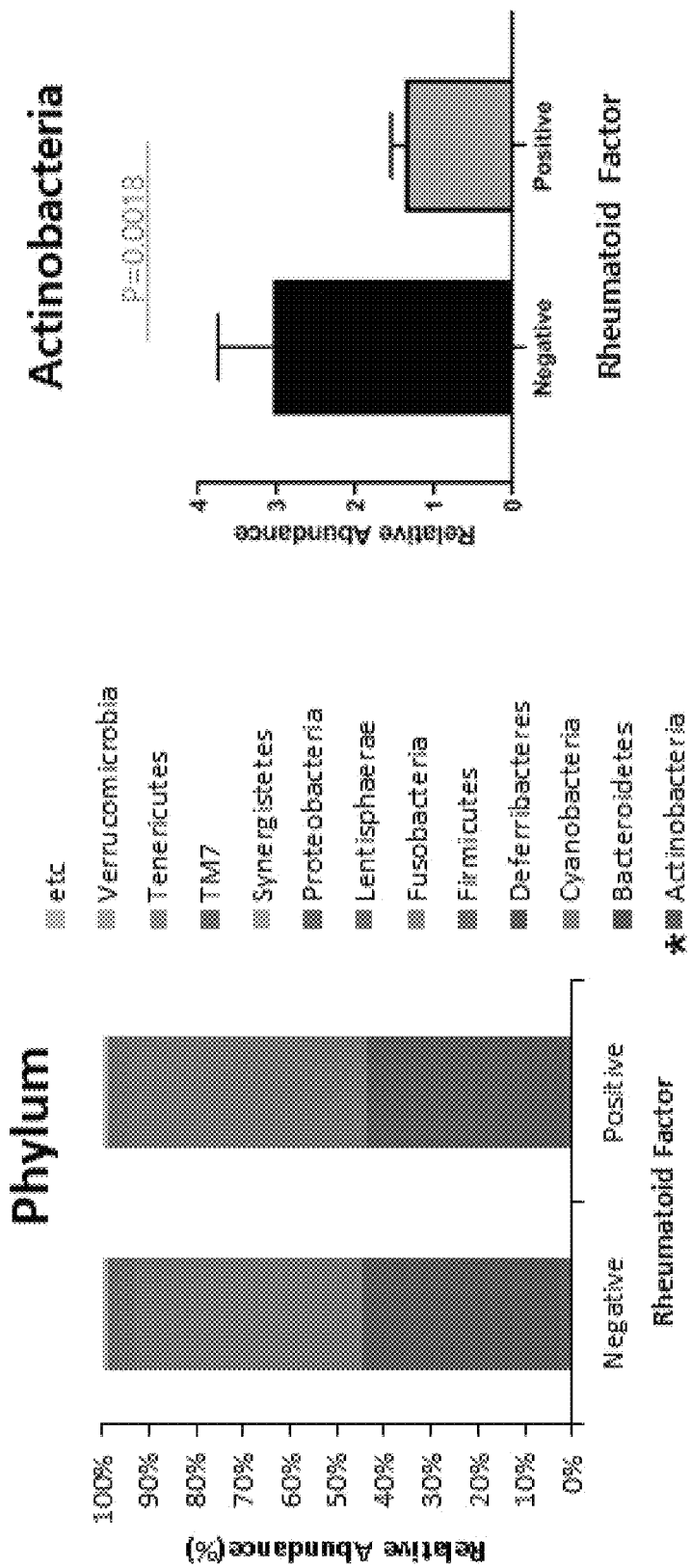
FIG. 1 is a graph showing the result of analysis of the intestinal flora distribution at the phylum level depending on the presence (negative/positive) of rheumatoid factor of Korean rheumatoid arthritis patients.

2) Determination of Intestinal Flora Distribution at Phylum Level in Korean Rheumatoid Arthritis Patients The intestinal flora distribution was analyzed at the phylum level depending on the presence (negative/positive) of RF antibodies in Korean rheumatoid arthritis patients. As shown in FIG. 1, the result showed that *Actinobacteria* showed a statistically significant difference (p value: 0.0018) and that the RF-positive group (1.37%) exhibited significantly reduced relative abundance compared to the RF-negative group (3.06%).

Figure 2:
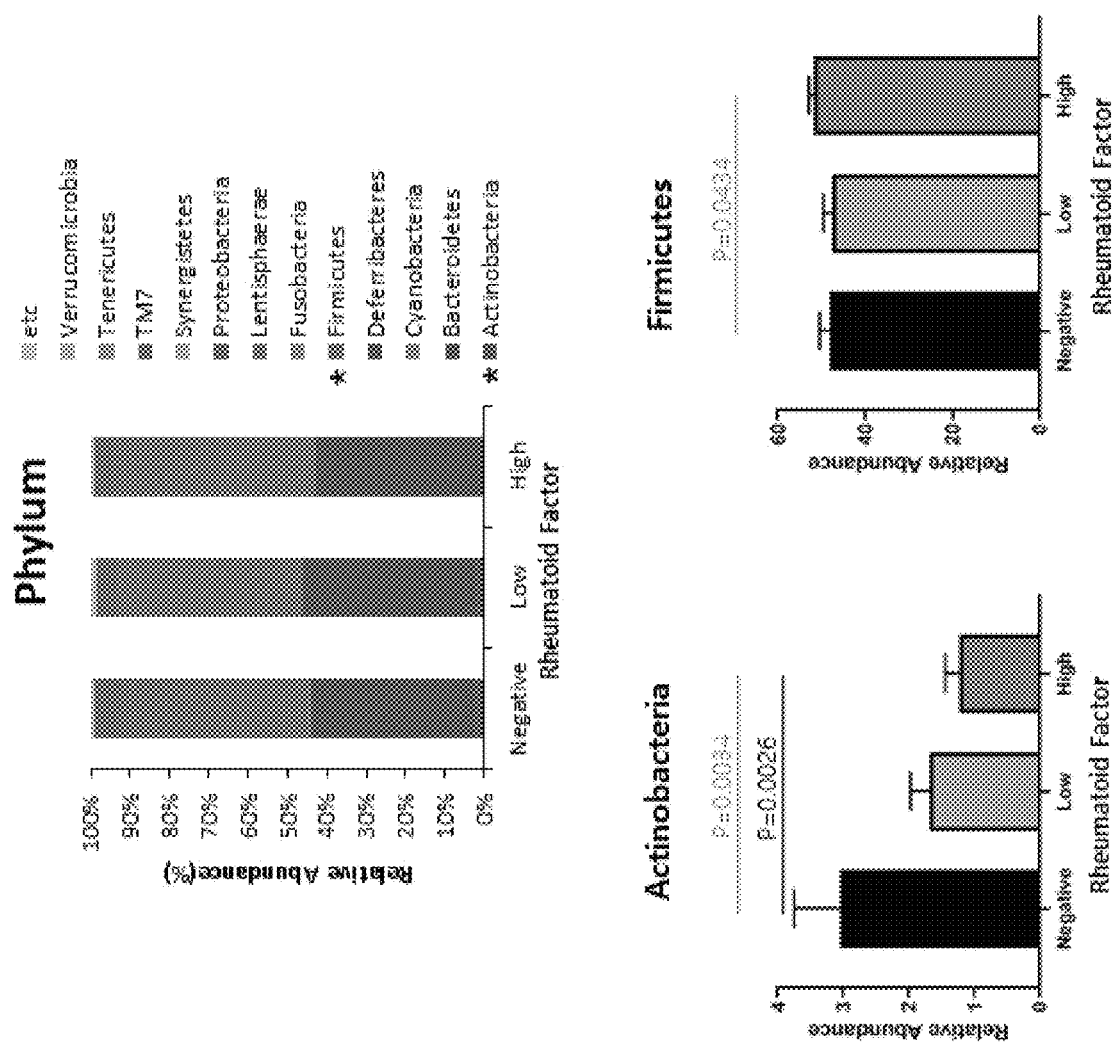
FIG. 2 is a graph showing the result of analysis of the intestinal flora distribution at the phylum level depending on the degree (negative/low positive/high positive) of rheumatoid factor of Korean rheumatoid arthritis patients.

In addition, the intestinal flora distribution was analyzed at the phylum level depending on the degree (negative/low positive/high positive) of RF antibody in Korean rheumatoid arthritis patients. As shown in FIG. 2, the result showed that *Actinobacteria* showed a statistically significant difference (p value: 0.0034), and the RF-high-positive group (1.23%) exhibited considerably reduced relative abundance than the RF-negative group (3.06%). In addition, as RF increased in *Actinobacteria*, relative abundance decreased in the order of RF-negative group (3.06%), RF-low-positive group (1.68%) and RF-high-positive group (1.23%). Firmicutes also showed a significant difference, but the magnitude of the difference was insignificant.

Figure 3:
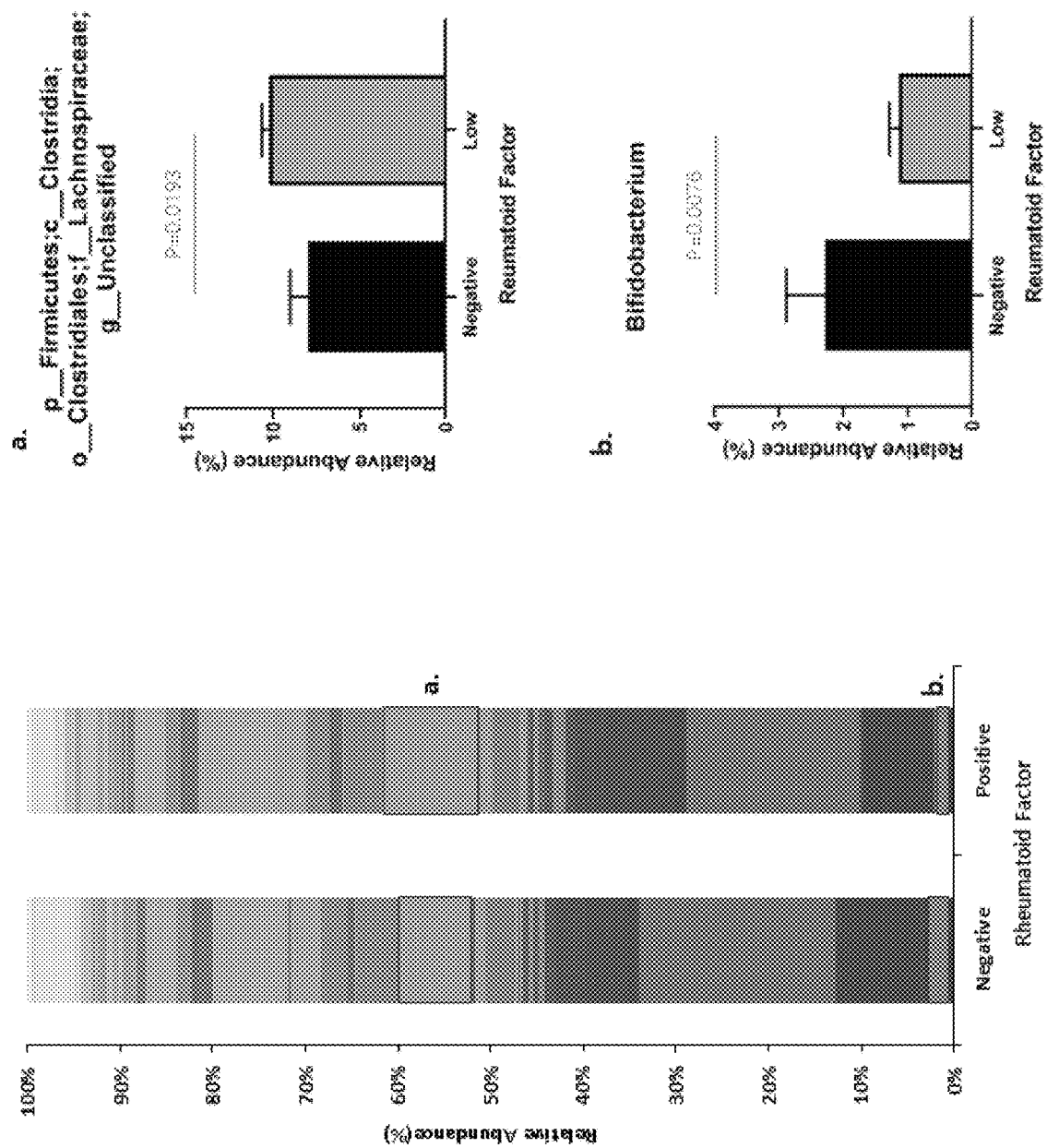
FIG. 3 is a graph showing the result of analysis of the intestinal flora distribution at the genus level depending on the presence (negative/positive) of rheumatoid factor of Korean rheumatoid arthritis patients.

3) Determination of Intestinal Flora Distribution at Genus Level in Korean Rheumatoid Arthritis Patients The intestinal flora distribution was analyzed at the genus level depending on the presence (negative/positive) of RF antibodies in Korean rheumatoid arthritis patients. As shown in FIG. 3, the result showed that *Bifidobacterium* and unclassified genus showed a statistically significant difference (p value: 0.0076, p value: 0.0193), and in the case of *Bifidobacterium*, the RF-positive group (1.14%) exhibited significantly reduced relative abundance compared to the RF-negative group (2.29%).

Figure 4:
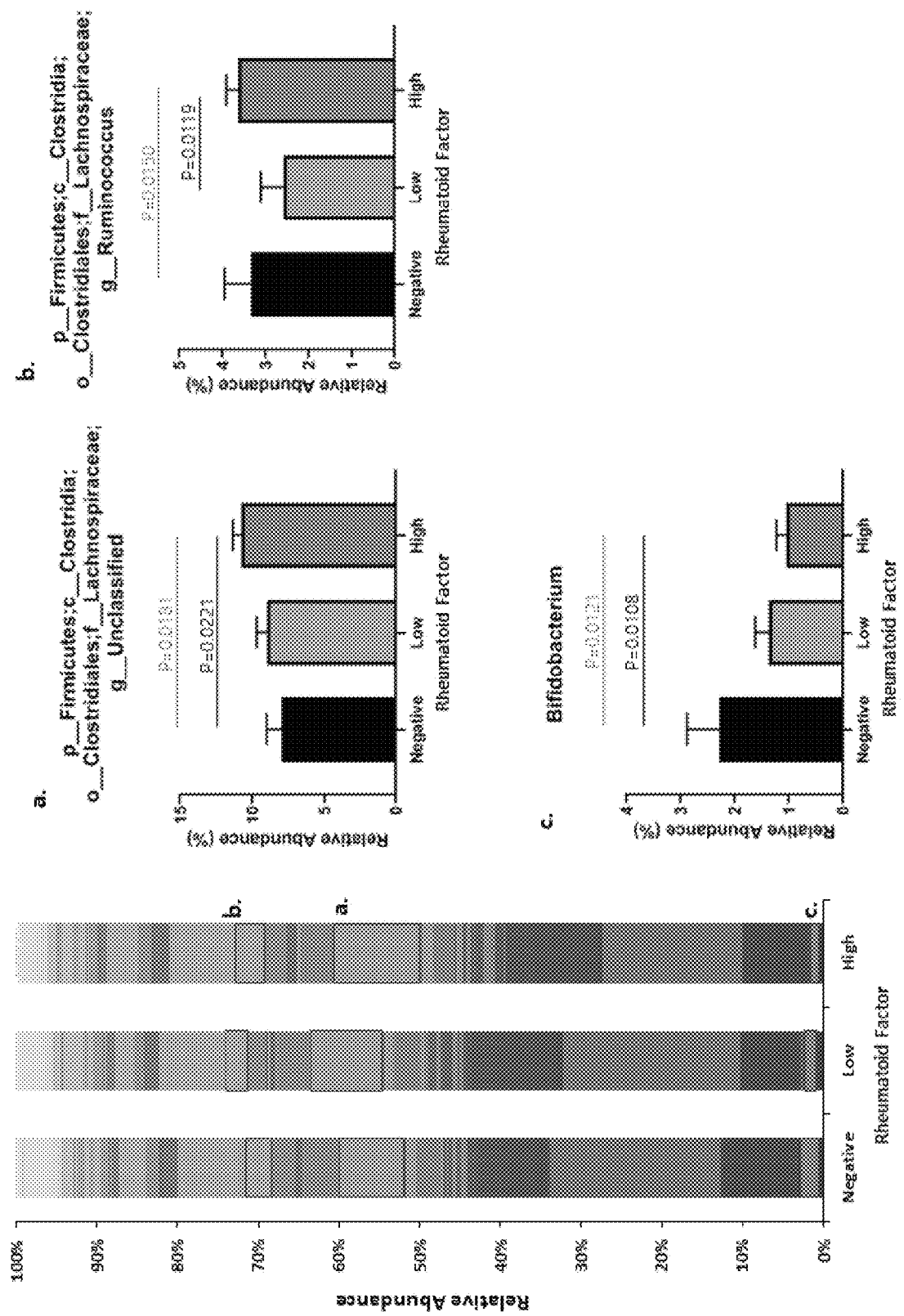
FIG. 4 is a graph showing the result of analysis of the intestinal flora distribution at the genus level depending on the degree (negative/low positive/high positive) of rheumatoid factor of Korean rheumatoid arthritis patients.

In addition, the intestinal flora distribution was analyzed at the genus level depending on the degree (negative/low positive/high positive) of RF antibody in Korean rheumatoid arthritis patients. As shown in FIG. 4, the result showed that the genus *Bifidobacterium*, which belongs to the phylum *Actinobacteria*, showed a statistically significant difference (p value: 0.0121), and the RF-high-positive group (1.04%) exhibited considerably reduced relative abundance than the RF-negative group (2.29%). In addition, as RF increased in *Bifidobacterium*, the relative abundance decreased in the order of the RF-negative group (2.29%), the RF-low-positive group (1.37%) and the RF-high-positive group (1.04%).

3) Isolation of *Bifidobacterium longum* RAPO (Accession No.: KCTC 13773BP)

Figure 5:
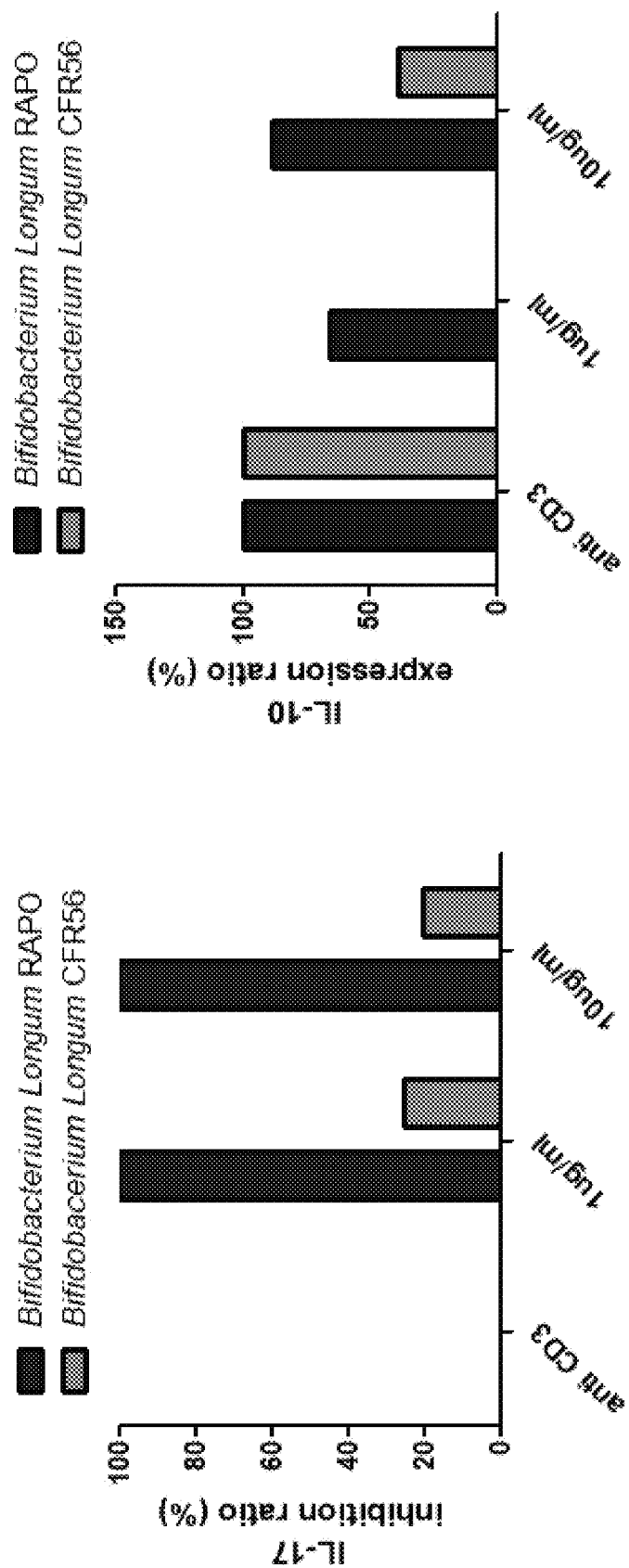
FIG. 5 is a graph showing the result of in-vitro experiments on *Bifidobacterium longum* RAPO identified in the present invention among several species of *Bifidobacterium*, wherein the graph shows the cytokine inhibition rate of *Bifidobacterium longum* RAPO of the present invention, based on expression levels, measured by ELISA, of cytokine IL-17, which is the cause of rheumatoid arthritis, and cytokine IL-10 inhibiting cytokine IL-17.

The present inventors have isolated several species of *Bifidobacterium* from rheumatoid arthritis patients and normal subjects. Among them, *Bifidobacterium longum* RAPO was selected as a strain having an excellent effect of inhibiting IL-17, which is a cytokine that has been identified as the cause of rheumatoid arthritis, and an excellent effect of maintaining and increasing IL-10, which is known to inhibit IL-17 (FIG. 5). In an attempt to induce activation of T-cell, as shown in FIG. 5, peripheral mononuclear cells from one normal subject, stimulated with antiCD3, were treated with 1 µg/ml and 10 µg/ml of *Bifidobacterium longum* RAPO of the present invention and cultured for 72 hours, and then, at the end of the experiment, IL-17 and IL-10 expression levels were measured using ELISA. The result showed that *Bifidobacterium longum* RAPO inhibited nearly 100% of the cytokine IL-17, which is considered to be the cause of rheumatoid arthritis, and maintained or increased IL-10, which means that *Bifidobacterium longum* RAPO has better immunomodulatory capability than other bacteria (*B. longum* CFR56 in FIG. 5).

Therefore, the *Bifidobacterium longum* RAPO selected in the present invention was deposited under accession number of KCTC 13773BP in the Korea Research Institute of Bioscience and Biotechnology on Dec. 11, 2018.

The results demonstrated that, as the autoantibody rheumatoid factor (RF) found in a number of rheumatoid patients increases, the amount of the genus *Bifidobacterium*, which belongs to the phylum *Actinobacteria*, decreases. Accordingly, *Bifidobacterium longum* RAPO (Accession No.: KCTC 13773BP) of the present invention, found to have the most excellent in-vitro experimental results associated with the expression rate of cytokine, which is identified as a cause of rheumatoid arthritis, was selected from several *Bifidobacterium* species and animal experiments were conducted to determine the benefits of supplementation with *Bifidobacterium longum* RAPO.

[Experimental Example 1: Determination of the Effect of *Bifidobacterium longum* RAPO (Accession No.: KCTC 13773BP)] on Control of Rheumatoid Arthritis Disease In this experimental example, in order to determine the effect of *Bifidobacterium longum* RAPO (Accession No.: KCTC 13773BP)] of Example 1 on the control of rheumatoid arthritis disease, a mixture of type II collagen (CII) and CFA (adjuvant) (1:1) was injected at a dosage of 50 µl (100 µg of CII per mouse) into the base of the tail of DBA/1J mice. Two weeks later, a mixture of CII and IFA (1:1) was secondarily injected at 100 µg/50 µl to produce arthritis animals. Three weeks after the onset of rheumatoid arthritis, 50 mg/kg of *Bifidobacterium longum* RAPO was orally administered daily. For comparison, a rheumatoid arthritis group not administered with *Bifidobacterium longum* RAPO (vehicle) and a methotrexate (a type of antirheumatic drug)-administered group (MTX) were prepared. Methotrexate was orally administered at 3 mg/kg.

Figure 6:
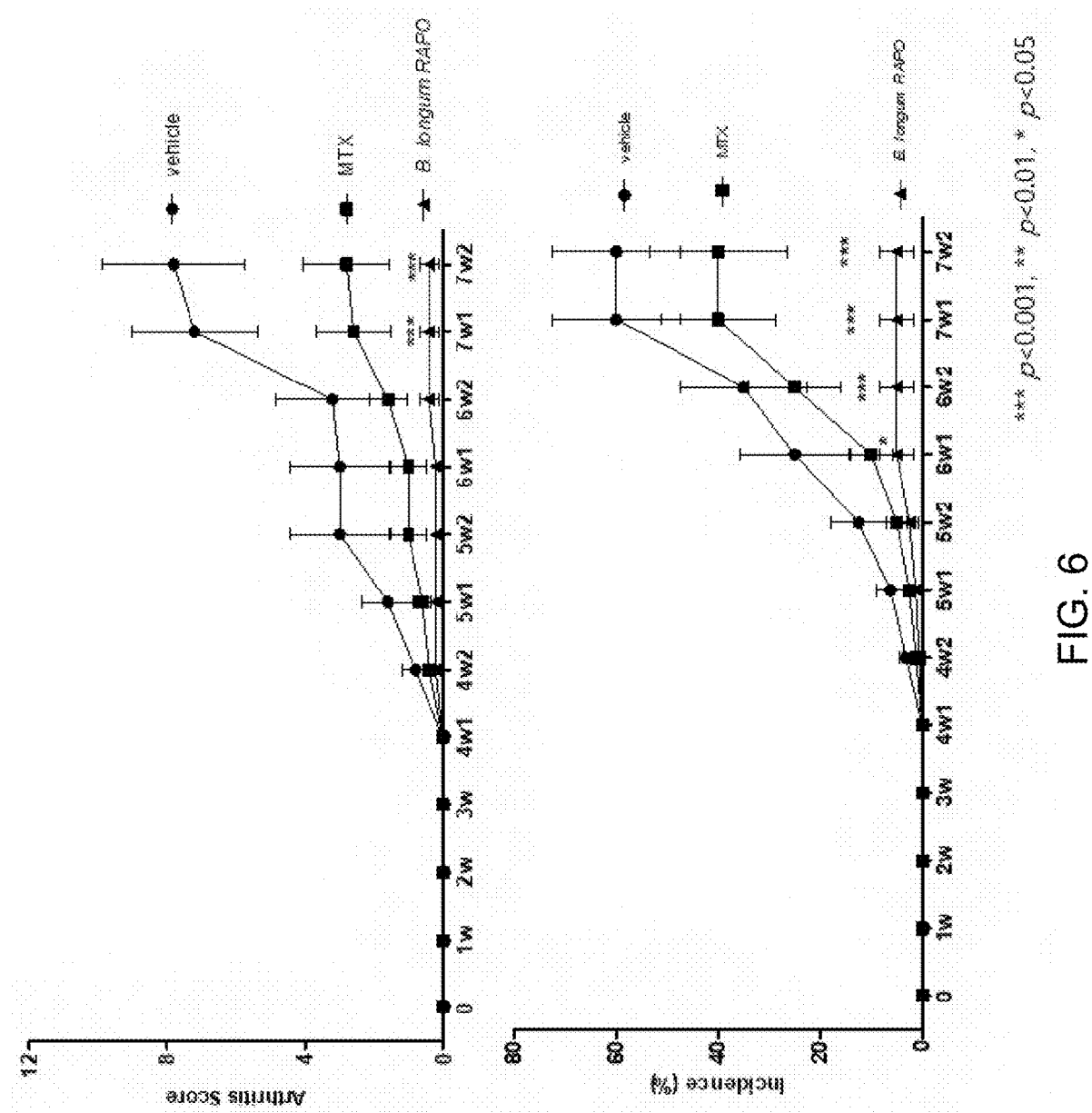
FIG. 6 is a graph showing the result of determination of the effect of *Bifidobacterium longum* RAPO (Accession No.: KCTC 13773BP) identified in the present invention on the control of rheumatoid arthritis disease (vehicle: rheumatoid arthritis group not administered with *Bifidobacterium longum* RAPO, MTX: methotrexate (MTX)-administered group, B. longum RAPO: *Bifidobacterium longum* RAPO-administered group). Rheumatoid arthritis incidence comparison (top), Rheumatoid arthritis incidence rate (bottom) (* $p<0.001$,  $p<0.01$, * $p<0.05$).

As shown in FIG. 6, the result showed that the methotrexate-administered group (MTX) and the *Bifidobacterium longum* RAPO-administered group (*B. longum* RAPO) exhibited better ability to inhibit the onset and the incidence rate of rheumatoid arthritis than the rheumatoid arthritis group not administered with *Bifidobacterium longum* RAPO (vehicle), and in particular, *Bifidobacterium longum* RAPO-administered group (*B. longum* RAPO) exhibited a significant inhibition. This indicates that *Bifidobacterium longum* RAPO has an effect of controlling rheumatoid arthritis disease.

Figure 7:
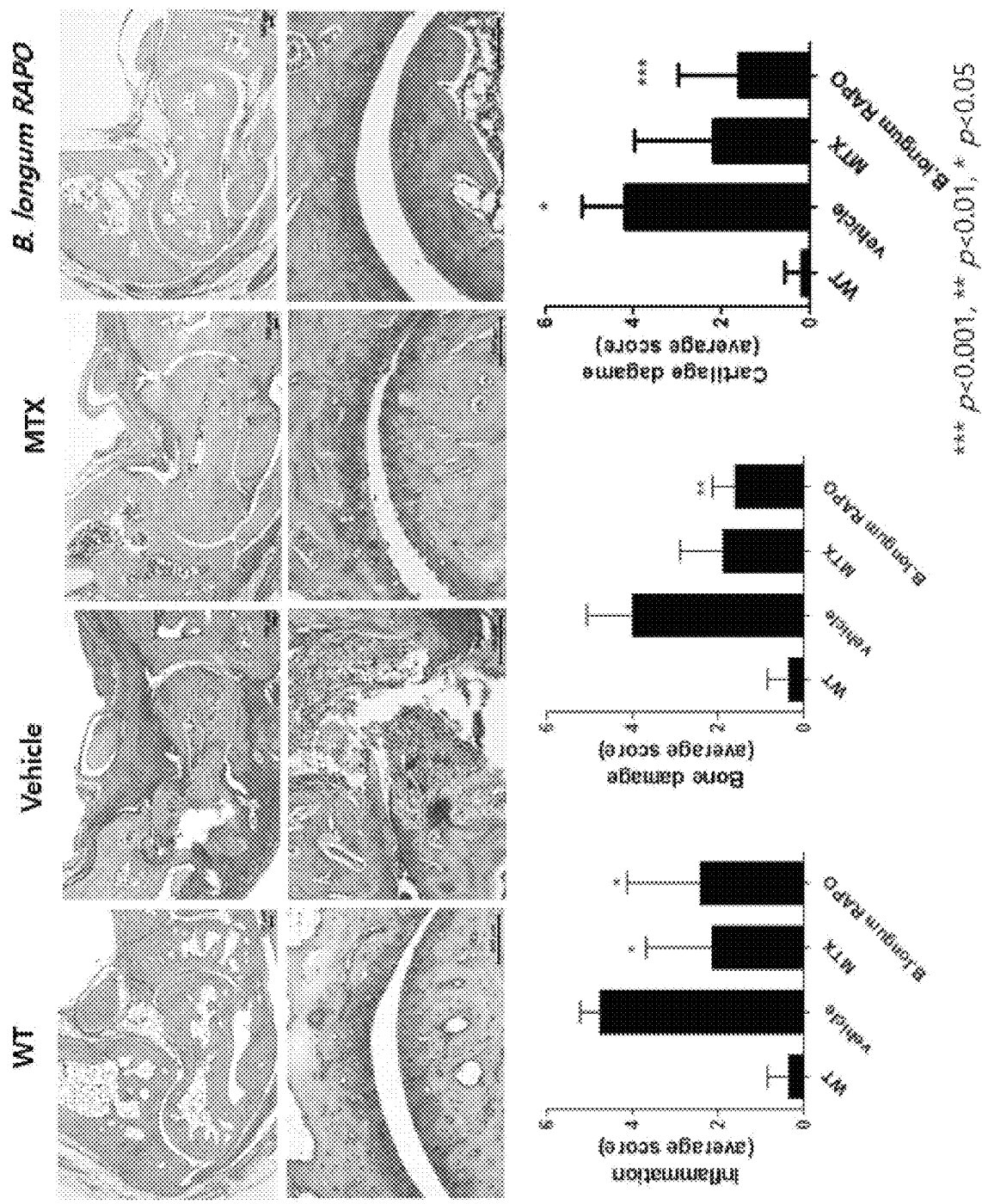
FIG. 7 is a graph showing the result of determination of the effect of *Bifidobacterium longum* RAPO (Accession No.: KCTC 13773BP) identified in the present invention on the control of joint tissue destruction (WT (wild type): normal group, vehicle: rheumatoid arthritis group not administered with *Bifidobacterium longum* RAPO, MTX: methotrexate (MTX)-administered group, B. longum RAPO: *Bifidobacterium longum* RAPO)-administered group) $p<0.001$, ** $p<0.01$, * $p<0.05$).

Experimental Example 2: Determination of Effect of *Bifidobacterium longum* RAPO (Accession No.: KCTC 13773BP) on Control of Rheumatoid Arthritis Joint Tissue Destruction In this experimental example, to determine the effect of the *Bifidobacterium longum* RAPO of Example 1 on rheumatoid arthritis joint tissue, the degree of damage to the joint tissue of the mice was analyzed. Based on the rheumatoid arthritis mouse group not administered with *Bifidobacterium longum* RAPO (vehicle), the mouse group administered with *Bifidobacterium longum* RAPO 50 mg/kg, the mouse group administered with methotrexate 3 mg/kg, and the normal wild-type (WT) mouse group not induced with rheumatoid arthritis (arthritis control group), normal (wild-type) group (WT), the rheumatoid arthritis group not administered with *Bifidobacterium longum* RAPO (vehicle), the methotrexate-administered group (MTX), and *Bifidobacterium longum* RAPO-administered group (*B. longum* RAPO) were subjected to Safranin O staining for analysis. As shown in FIG. 7, the result showed that the *Bifidobacterium longum* RAPO-administered group (*B. longum* RAPO) exhibited statically significant decreases in all of the degree of inflammation, and the degree of destruction of bone and cartilage, compared to the rheumatoid arthritis group not administered with *Bifidobacterium longum* RAPO (vehicle), which means that *Bifidobacterium longum* RAPO had an effect of controlling the destruction of rheumatoid arthritis joint tissue.

Experimental Example 3: Determination of Effect of *Bifidobacterium longum* RAPO (Accession No.: KCTC 13773BP) on Intestinal Damage Control In this experimental example, in order to evaluate the effect of *Bifidobacterium longum* RAPO on the control of intestinal damage, the degree of colorectal tissue damage of the mice was determined.

Figure 8:
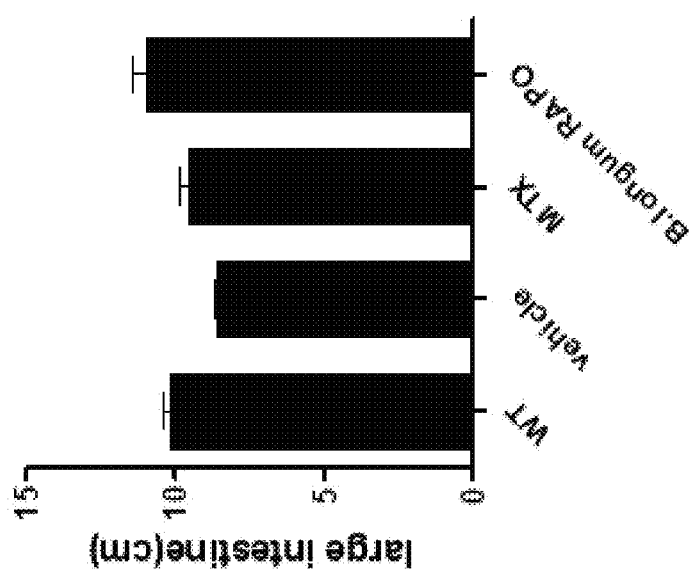
FIG. 8 is an image and a graph showing the result of determination of the effect of *Bifidobacterium longum* RAPO (Accession No.: KCTC 13773BP) identified in the present invention on the control of intestinal injury (WT (wild type): normal group, vehicle: rheumatoid arthritis group not administered with *Bifidobacterium longum*
Figure 8:
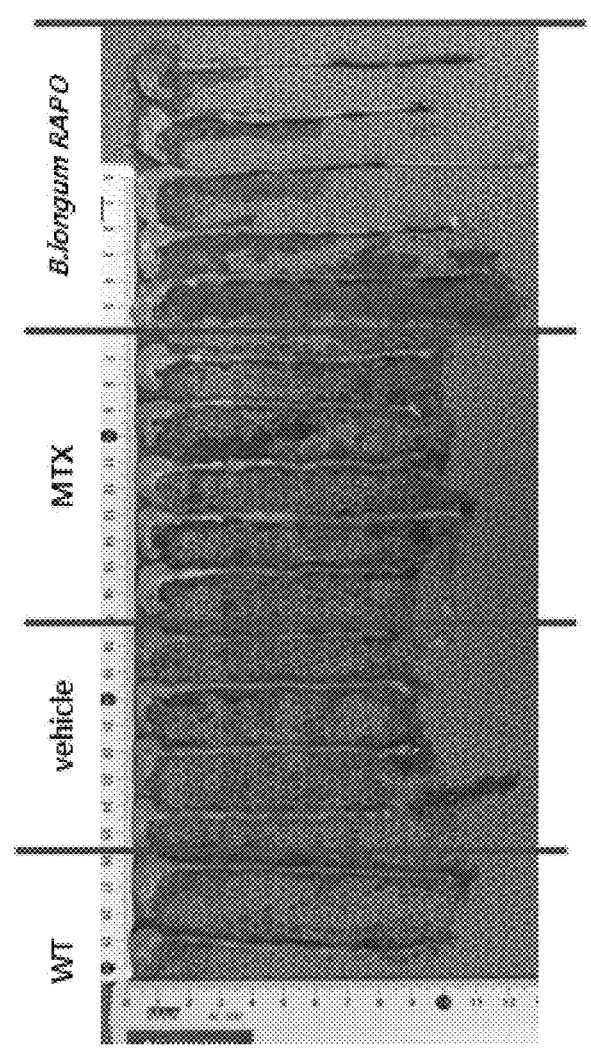

Based on the rheumatoid arthritis mouse group not administered with *Bifidobacterium longum* RAPO (vehicle), the mouse group administered with *Bifidobacterium longum* RAPO 50 mg/kg, the mouse group administered with methotrexate 3 mg/kg, and the normal wild-type (WT) mouse group not induced with rheumatoid arthritis (arthritis control group), normal (wild-type) group (WT), the rheumatoid arthritis group not administered with *Bifidobacterium longum* RAPO (vehicle), the methotrexate-administered group (MTX) and *Bifidobacterium longum* RAPO-administered group (*B. longum* RAPO) were investigated to determine colorectal tissue damage through comparison in colon length. As shown in FIG. 8, the result showed that the *Bifidobacterium longum* RAPO-administered group (*B. longum* RAPO) exhibited less colorectal tissue damage than the rheumatoid arthritis group not administered with *Bifidobacterium longum* RAPO (vehicle), which means that *Bifidobacterium longum* RAPO has an effect of controlling colorectal damage.

Experimental Example 4: Determination of Human Immune Cell Regulation Capability of *Bifidobacterium longum* RAPO (Accession No.: KCTC 13773BP)

In this experimental example, in order to evaluate the human immune cell regulation capability of the *Bifidobacterium longum* RAPO, the expression levels of inflammatory cytokine IL-17 and anti-inflammatory cytokine IL-10, affecting autoimmune diseases such as rheumatoid arthritis, were measured.

Peripheral blood mononuclear cells (PBMC) of normal subjects activated with anti-human CD3 (induced T-cell activity) were treated with 1 µg/ml of *Bifidobacterium longum* RAPO, and the amounts of expressed inflammatory cytokine IL-17 and anti-inflammatory cytokines IL-10 were measured by ELISA. For comparison, the rheumatoid arthritis group not administered with *Bifidobacterium longum* RAPO (vehicle) was used. As shown in FIG. 9, the result showed that *Bifidobacterium longum* RAPO-administered group (*B. longum* RAPO) had an inflammatory cytokine IL-17 inhibition rate of about 80% and an anti-inflammatory cytokine IL-10 inhibition rate of less than about 10%.

Experimental Example 5: Determination of Ammonia Generation Capability of *Bifidobacterium longum* RAPO (Accession No.: KCTC 13773BP)

In the present experimental example, the ammonia-generating ability was measured to determine the properties and stability of the *Bifidobacterium longum* RAPO of Example 1.

For this purpose, an indophenol method, which is a well-known method for analyzing the concentration of ammonia ($NH_3$), was used. This is a method for quantifying the amount of ammonia produced by measuring the absorbance of indophenol, which is produced by the reaction of ammonium ions in an analytical sample solution with phenol and sodium hypochlorite. As shown in FIG. 10, the result showed that *Enterococcus faecium*, a positive control group, produced 109.28 mg/L of ammonia, whereas *Bifidobacterium longum* RAPO did not produce ammonia.

Experimental Example 6: Determination of Hemolytic Property of *Bifidobacterium longum* RAPO (Accession No.: KCTC 13773BP)

In the present experimental example, in an attempt to determine the characteristics and stability of the *Bifidobacterium longum* RAPO of Example 1, hemolytic property thereof was determined.

For this purpose, *Listeria ivanovii*, as a positive control group, and *Bifidobacterium longum* RAPO were streaked on a plate prepared by adding 5% sheep blood to a BHI agar medium, and hemolysis was observed. β-hemolysis was considered to occur when the stretched surrounding area became transparent. As shown in FIG. 11, the result showed that *Listeria ivanovii*, as a positive control group, was found to cause hemolysis, whereas *Bifidobacterium longum* RAPO was found to cause no hemolysis even after triplicate-repeated experiments.

The results described above demonstrated that the novel *Bifidobacterium longum* RAPO (Accession No.: KCTC 13773BP) has an effect of controlling rheumatoid arthritis by inhibiting the onset and incidence rate of rheumatoid arthritis, and has an effect of controlling the destruction of rheumatoid arthritis joint tissue by reducing the degree of inflammation and destruction of bones and cartilage. In addition, the strain controls the colorectal tissue, inhibits the inflammatory cytokine IL-17, affecting the onset of rheumatoid arthritis, and has neither ammonia production ability nor hemolytic ability, which means that the strain is safe and effective for alleviating, preventing or treating rheumatoid arthritis, and can be incorporated in a composition.

The present inventors deposited *Bifidobacterium longum* RAPO (Accession No.: KCTC 13773BP) at the Korea Research Institute of Bioscience and Biotechnology.

Depositary: Korea Research Institute of Bioscience and Biotechnology

Accession No.: KCTC 13773BP

Date of deposition: Dec. 11, 2018

The invention claimed is:

1. A food composition for alleviating rheumatoid arthritis comprising at least one selected from the group consisting of a culture solution comprising *Bifidobacterium longum* RAPO (Accession No.: KCTC 13773BP), a concentrate of said culture solution and a dry powder of said culture solution.

2. The food composition according to claim 1, wherein the food composition comprises any one selected from lactic-acid-bacteria-fermented milk, soy milk, milk powders, yogurts, beverages, granules and health supplements.

3. A pharmaceutical composition for preventing or treating rheumatoid arthritis comprising at least one selected from the group consisting of a culture solution comprising *Bifidobacterium longum* RAPO (Accession No.: KCTC 13773BP), a concentrate of said culture solution and a dry powder of said culture solution.

* * * * *